United States Patent [19]

Roxlo et al.

[11] Patent Number: 4,690,750
[45] Date of Patent: Sep. 1, 1987

[54] MICRO-POROUS SUPERLATTICE SEPARATIONS

[75] Inventors: Charles B. Roxlo, Bridgewater; Harry W. Deckman, Clinton, both of N.J.

[73] Assignee: Exxon Research and Engineering Company, Florham Park, N.J.

[21] Appl. No.: 874,027

[22] Filed: Jun. 13, 1986

[51] Int. Cl.⁴ .................................................. C07C 7/12
[52] U.S. Cl. ........................... 208/310 Z; 585/820; 55/423; 55/529; 55/263; 148/DIG. 160; 422/222
[58] Field of Search ................ 208/310 Z, 310 R; 585/820; 55/74, 75, 389, 512, 522, 523, 529; 422/312, 177, 180, 211, 219, 222; 210/263, 282; 148/DIG. 160

[56] References Cited

U.S. PATENT DOCUMENTS

| | | | |
|---|---|---|---|
| 4,159,284 | 6/1979 | Seko et al. | 208/310 Z |
| 4,324,701 | 4/1982 | Honda et al. | 422/222 X |
| 4,509,966 | 4/1985 | Dimick et al. | 55/523 X |
| 4,521,236 | 6/1985 | Yamamoto et al. | 55/523 X |
| 4,598,164 | 7/1986 | Tiedje et al. | 148/DIG. 160 X |

*Primary Examiner*—Andrew H. Metz
*Assistant Examiner*—Glenn Caldarola
*Attorney, Agent, or Firm*—Ronald D. Hantman

[57] ABSTRACT

A high surface area substrate with controlled pore size and slot geometry is used in an adsorbing process. The material is made by depositing at least two materials in alternating layers. The film is then broken up and one of the materials is etched away to produce a slotted surface structure. These slots can add size and shape selectivity to separations and catalytic processes which because of the uniform and controllable dimensions (>5A) would be superior to that obtainable from zeolites and clays.

10 Claims, 14 Drawing Figures

MICRO-POROUS SUPERLATTICE SEPARATIONS

BACKGROUND OF THE INVENTION

Materials with controlled size pore structure on the atomic dimension have been used as molecular sieves for sorption, catalysts, and ion exchange resins. The most well known of these materials are zeolites which is a name derived from the Greek, meaning boiling stones. The controlled pore structure of zeolites result from the chemical arrangement of $(Al,Si)O_4$ tetrahedra which share all their oxygen vertices with nearby tetrahedra and are joined together to give rise to large cavities and controlled size windows into these cavities. The alumino-silicate framework forming the zeolite usually has a negative charge which is balanced by alkalies and alkaline earths located outside the tetrahedra in the channels. These materials have proven to be useful in a variety of industrial applications because of the shape and chemistry of the pore structures formed by the linked alumino silicate tetrahedra. Pores in these materials can be monodisperse and small enough to act as molecular sieves so that different apparent surface areas are obtained according to the size of the absorbate molecules. The chemistry of the framework and the counter ions neutralizing electrical charge on the framework can have many catalytic applications. In particular, the controlled pore structure can produce shape selective effects in catalysis (see, e.g., N. Y. Chen, U.S. Pat. No. 3,630,966, Dec. 28, 1971).

In all zeolites, the chemical composition is intimately related to the size of the pore structure. Maximum pore size in zeolites is related to the geometric arrangement of the alumino-silicate tetrahedra and is always less than about 10 Å.

The present invention describes zeolite like materials for use as molecular sieves. These materials are made using physical fabrication techniques. Physical fabrication techniques such as etching, deposition and lithographic patterning have been extensively used for the production of microelectronics. Features with approximately one micron critical dimensions are routinely created using these methods for microelectronic circuitry; however, to produce porous materials capable of molecular sieving requires reducing the feature size by three orders of magnitude.

Reduction in feature size is obtained by using new methods for defining the pattern used with thin film etching and deposition techniques. By using physical fabrication techniques to produce controlled porosity on the molecular dimension, new degrees of freedom in constructing zeolite like materials are obtained. Physical fabrication techniques decouple the interrelationship between size and chemistry of the pore structures. Thus, the composition of zeolite like materials made with physical fabrication techniques is not limited to aluminosilicates. Using the physical fabrication techniques described herein it is possible to make zeolite-like materials from a wide variety of semiconductors, metals and insulators. Shape of pore structures made with physical fabrication techniques can be significantly different from those in natural and synthetic aluminosilicate zeolites. For example, the pore structure occurring in the physically fabricated etched superlattice structure described herewith is two dimensional rather than one dimensional as is the case for conventional zeolite materials. Precise control of pore size can be obtained using physical fabrication allowing for a choice of critical dimensions in the size range from approximately 10 to more than 10,000 Å. This is a size range not readily accessible with conventional zeolite materials. With these broad ranges of flexibility of construction, etched superlattice zeolite-like materials made by physical fabrication techniques have a control over pore size and chemistry which is not available with conventional aluminosilicate zeolites. Since pore size and chemistry are the determining factors in use of zeolites for separations and catalysis, etched superlattice zeolite-like materials will have many inherent advantages in these areas. In particular, etched superlattices provide a new class of micro-porous shape selective materials that significantly expand the range of behavior spanned by conventional zeolites. The term "shape selective" or "shape selective activity" is taken throughout this patent to mean a material whose interaction with chemical molecules can be different depending on the molecular size or shape.

SUMMARY OF THE INVENTION

The present invention is a process for absorbing a molecular species from a medium comprising contacting the medium with a superlattice which includes a multilayered material having layers which extend laterally with different dimensions so as to provide two dimensional slots within the multilayered material.

Absorption includes the penetration of the molecular species into the inner structure of the superlattice as well as adherence of the species to the surface of the superlattice.

In preferred embodiments, the medium may be a liquid or a gas. The molecular species may be organic, a hydrocarbon or aromatic. Specific examples include tetracene, pyrene, anthracene, naphthalene, rubene and dipyrenyl decane.

The absorption of the species onto or into the superlattice separates the species from the medium. Removing the superlattice from the medium then removes the species from the medium. The absorption of the species by the superlattice may depend on the size or shape of species. For example, a smaller molecule may be separated from a larger molecule by the smaller molecule preferentially entering the slots of the superlattice.

BRIEF DESCRIPTION OF THE DRAWINGS

FIG. 1 shows a schematic diagram of a fabrication sequence used to create controlled dimension pores in superlattice zeolite-like materials.

FIG. 2 illustrates the use of an interfacial layer for removing a pre-divided superlattice film from a substrate.

DESCRIPTION OF THE PREFERRED EMBODIMENT

A. Preparation of Superlattice Absorbers

Figure 1A:
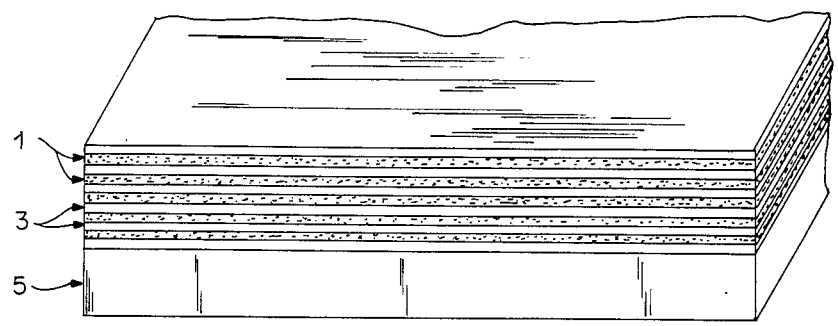
FIG. 1a shows a schematic representation of a superlattice composed of two alternating layers deposited on a substrate.
Figure 1B:
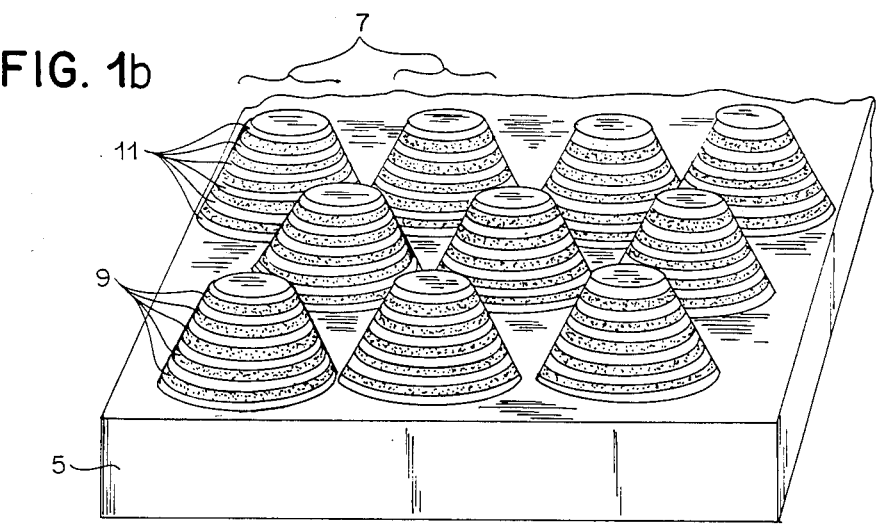
FIG. 1b shows a schematic representation of a superlattice of FIG. 1a after it has been divided into cylindrical post structures.
Figure 1C:
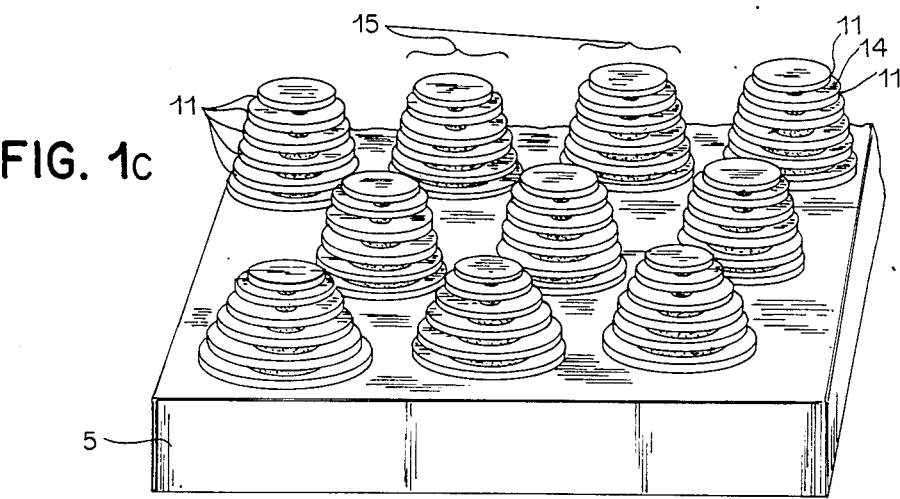
FIG. 1c shows a schematic representation of a microporous superlattice material formed by selectively etching the exposed layers shown in FIG. 1b.

Superlattices consisting of thin film layers 5–2500 Å thick, provide a unique template for forming two dimensional pores with precisely controlled surface chemistry. By breaking the thin film up in a manner that exposes edges of the thin film layers it is possible to create a slotted structure by selectively etching away one or more of the materials comprising the superlattices. FIG. 1 shows a schematic diagram of a fabrication sequence used to create controlled dimension pores in superlattice zeolite-like materials. In the sequence shown in FIG. 1 alternating thin film layers 1,3 are sequentially deposited onto a substrate 5. The lithographic template formed by the alternating layers 1,3 is exposed by patterning cylindrical post structures, 7 into the film surface. The layers exposed at the edge of the post 9,11 form the pattern used to delineate slots in a selective etching process. When one of the layers 9 exposed at the post edge is selectively etched, slots 13 are formed in the post and the material containing the array of etched slots is referred to as a micro-porous superlattice material 15. The width and uniformity of the resulting slot is determined by the thickness and uniformity of the deposited film. Since superlattices can be grown with layers that are flat and smooth to better than 5 Å, (P. N. Petroff, A. C. Gossard, W. Weigmann and A. Savage, J. Cryst. Growth 44, 5 [1978]; H. W. Deckman, J. H. Dunsmuir and B. Abeles, Appl. Phys. Lett. 46, 171 [1985]) the resulting slot structure can be smooth on atomic dimensions. Width of the slot can be as small as 5 Å, which is comparable to the size of many small organic molecules. Larger size two dimensional pores can be produced from thicker layers to accommodate larger molecular species. Chemistry of the slots can be directly controlled by the choice of materials used to form the superlattice.

Superlattice materials have interesting physical and electrical properties (including quantum wells) which are not relevant for the present invention. As used herein, superlattice materials are layered materials in which the interfaces between layers are sufficiently abrupt and smooth so that if the layer thicknesses are made small enough, quantum wells would be observed.

For superlattices composed of two alternating layers, the walls and ends of the slot will usually have different chemical behavior. This offers unique possibilities for designing synthetic etched superlattice zeolites in which shape selective absorption is decoupled from chemical reactions which can be catalyzed by the material forming the slot end. Moreover superlattice structures composed of three sequentially alternating layers provide the opportunity for producing different chemistry on the two faces as well as ends of the slots. This approach to the formation of shape selective materials offers unparalleled freedom in choosing size and surface functionality of the porous material to optimize the performance as a molecular sieve.

Specific surface area for sorption ($M^2/gm$) in etched superlattices can be accurately adjusted during fabrication. Depending on the characteristic thickness $t_1$ and $t_2$ ... $t_n$ of individual layers and the fraction (f) of the characteristic length (D) of each layer that is etched, specific surface areas can be adjusted to be in the range of 0.001–2,500 $M^2/gm$. For superlattices divided and etched in the manner shown in FIG. 1, the specific surface area for sorption, S, is $$S(M^2/gm) = \frac{4f(1 - f/2)}{t_1\rho_1 + t_2\rho_2(1 - f)^2} \quad (1)$$

where $\rho_1$ and $\rho_2$ are the density of the unetched and etched layers, respectively, and $t_1$ and $t_2$ are the corresponding layer thicknesses. In this case the layer length is equal to the post diameter D and the depth l of the slot etched into the edge of the post is $l = fD/2$ where f is the fractional etched length of superlattice in each post. When f is less than 1/5, Eq. 1 can be approximated as $$S(M^2/gm) \approx \frac{4f}{t_1\rho_1 + t_2\rho_2}. \quad (2)$$

and it is seen that the specific surface area varies linearly with the fractional length of superlattice etched. To obtain materials with large specific surface areas (in excess of $0.1 M^2/gm$), it is desirable to have f > 1/40. An approximately equivalent statement of this condition which is also preferred is to have the maximum lateral extent of the etched layers (D−2l) be less than forty times the length of the slots, l. In a more preferred embodiment, which produces high specific surface areas (10–2500$M^2/gm$) f is greater than ¼. This condition can be restated in the following more preferred form, which is that the maximum extent of the etched layers (D−2l) is less than 4 times the slot length, l. When the superlattice is divided into irregularly shaped particles, D is taken to be an average length of each layer and l is taken as the average effective slot depth; and the fractional slot depth f is defined as f = 2l/D. When more than two layers comprise the repeat unit of the superlattice, then the preferred conditions are taken to apply to the etched layers.

Superlattices of semiconductors, metals and insulators have been produced using a wide variety of deposition techniques. These materials were originally produced to study optical, electronic and magnetic properties of stacks of ultra-thin layers. Initially, superlattices were made from crystalline semiconductors by molecular beam epitaxy (seem for example, L. Esaki and R. Tsu, I.B.M. J. Res. Dev. 14, C1 (1970), A. C. Gossard, Thin Solid Films); a procedure which made very perfect films, but which was suited only for the production of small areas and limited volumes. with the expansion of interest in superlattice materials several other deposition techniques have been used to grow smooth sequential layers with abrupt interfaces. Techniques which have been used to produce superlattices include chemical vapor deposition, sputtering and evaporation. Most recently, it has been shown that plasma enhanced chemical vapor deposition can be used to produce superlattices of tetrahedrally bonded amorphous materials (B. Abeles and T. Tiedje, Phys. Rev. Lett. 51, 2003 (1983)) such as a—Si:H, a—Ge:H, a—Si$_{1-x}$C$_x$:H, a—SiO$_x$:H or a—SiN$_x$:H. A key requirement for all of these deposition techniques is that the superlattice be deposited at a temperature below which interdiffusion of the layers occurs. Anothe requirement is that the surface mobility of the depositing species be such that the layers do not grow as islands but rather grow as flat smooth continuous films.

Alternating layers ae formed in evaporation and sputter deposition processes by sequentially translating a substrate in front of two or more deposition sources. The thickness of each layer is determined by the time each substrate is held in front of a deposition source as well as by the rate of deposition. In plasma assisted chemical vapor deposition alternating layers are formed by sequentially changing the reactive gases flowed through the plasma reactor. In this case, deposition time and rate directly determine the thickness of each layer. Layer composition is determined by choice of reactive gases for plasma assisted chemical vapor deposition and source composition for sputtering and evaporation. The independent control of layer spacing and composition offered by these techniques provides a degree of freedom in designing a molecular sieve which is not available with zeolites or clays. This degree of freedom also allows for making multilayered materials with predetermined thickness in each layer as well as with compositional variations in different layers which do not necessarily form a simple repeat structure.

For purposes of illustration of the present invention, the following discussion shall describe one embodiment wherein the superlattice material includes layered material having a repeat distance wherein each repeat distance includes two or more layers. The composition of each repeat is then repeated throughout the superlattice. Since the methods for fabricating superlattices allow for adjustments of composition and thickness of each individual layer, the word repeat is taken to mean a characteristic unit of substantially similar thickness and/or composition. It is noted that sequential repeat units can have intentionally introduced differences which do not substantially affect the performance of etched superlattice zeolite-like materials in particular process applications.

To etch slots into the superlattice material, deposited films must be divided in a manner that exposes the edges of the thin film layers comprising the superlattice. A number of different methods are available for breaking the film up without delaminating the layers. Methods of dividing the film to expose the layer edges include grinding, pulverizing, and lithographic patterning. Of these, lithographic patterning techniques can produce the most uniform particle sizes. For lithographic patterning, a mask is deposited on the surface of the superlattice with a pattern which defines the shapes of the particles to be created. The pattern is transferred from the mask into the underlying superlattice by differentially etching the superlattice with respect to the mask. This process divides the superlattice film into individual particles whose lateral dimensions are determined by the geometry of the mask. For example, the film can be divided into cylindrical posts by using a sub-monolayer of spherical colloidal particles as an etch mask (Natural Lithographic Fabrication of Microstructures over Large Areas, H. W. Deckman and J. Dunsmuir, U.S. Pat. No. 4,406,695). Diameter of the resulting post is determined by the colloidal particle diameter and the directionality of the etch used to transfer the pattern on the surface of the film. If the pattern transfer is from an anisotropic etch, the diameter of the resulting post will closely correspond to that of the particulate etch mask. Anisotropic etches which can be used to faithfully transfer the pattern of the spherical mask include ion beam etching and directional reactive ion etching with the plasma. Although lithographic patterning can produce the most uniform particle size, it is in some cases desirable to divide the film using physical fracture methods such as grinding and pulverizing. In this case the particle size is determined by the detailed abrasion method used, although typically particles will have dimensions greater than 1 $\mu$m.

In general, it is preferable to minimize the particle size in the divided film. By minimizing particle size, smaller fractional etch lengths, f, can be used to make high surface area materials. The surface area in the etched superlattice structure varies linearly with the number of layers exposed in the divided film structure. To produce high surface area materials, it is preferred that the multilayered superlattice include at least 5 layers and it is more preferred for it to include at least 25 layers. Furthermore, it is preferred that at least this number of layers be exposed at the edge of the divided film structure.

Figure 2A:
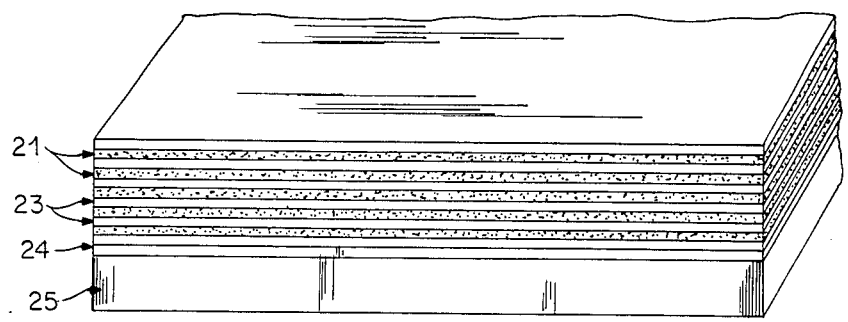
FIG. 2a shows a schematic representation of a superlattice deposited on a substrate coated with interfacial release layers.
Figure 2B:
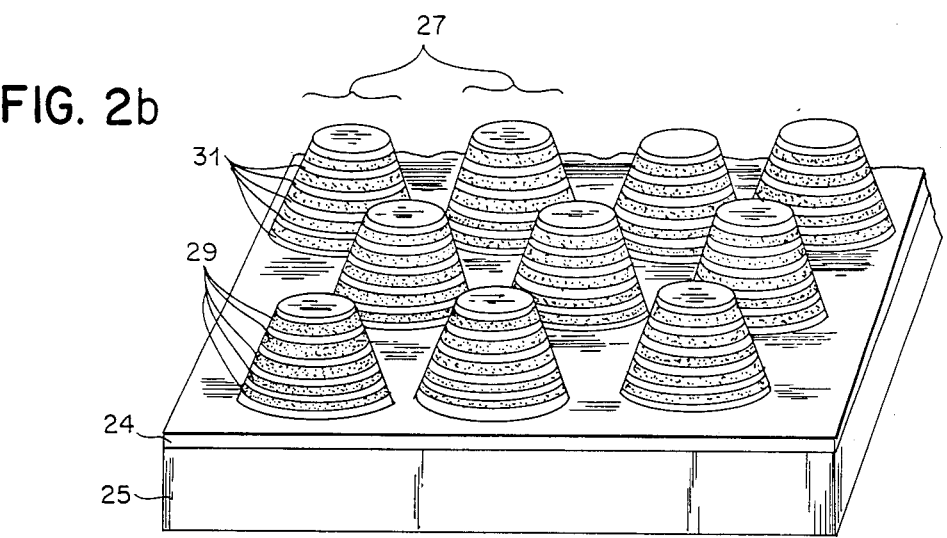
FIG. 2b shows a schematic diagram of the superlattice shown in FIG. 2a after it has divided in the form of cylindrical post structures.
Figure 2C:
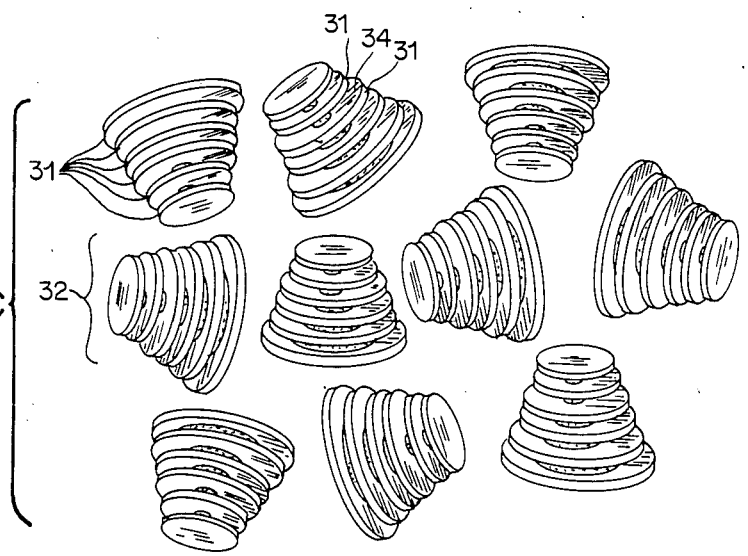
FIG. 2c shows a schematic representation of a free standing microporous superlattice material formed by selectively etching exposed superlattice shown in FIG. 2b and dissolving the interfacial release layer.

In some cases it is desirable to remove the film from the substrate when it is divided to expose layer edges. The substrate can be removed by dissolving it in an etchant which does not attack the superlattice. For instance, superlattices composed of silicon and silicon nitride can be removed from glass or quartz substrates by etching in a hydrofluoric acid bath. Dissolution of a superlattice film from a substrate can often be aided by use of an interfacial layer. FIG. 2 illustrates the use of an interfacial layer 24 for removing a pre-divided superlattice film from a substrate. The substrate 25 is first coated with a thin interfacial layer 24 before the layers of the superlattice 21 and 23 are deposited. It is possible to remove the superlattice film from the substrate by simply dissolving the interfacial layer before or after dividing. In FIG. 2 the film is removed after dividing. The superlattice film shown in FIG. 2 is lithographically divided into cylindrically symmetric post structures, 27, exposing edges of the layers 29 and 31. The interfacial layer 24 can then be dissolved either before or after slots 23 are etched into the particles 27. After dissolution of the interfacial layer 24, the etched particles of the superlattice that are lifted off the substrate 25 form an etched micro-porous superlattice material, 31. For instance, a silicon/silicon dioxide superlattice can be removed from a glass substrate by etching away an interfacial coating of aluminum. The thickness of the interfacial layer should be such that the etchant can readily diffuse to lift the superlattice film away from the substrate.

Slot structures are formed by selectively etching the exposed edges, 9, 11, 29 and 31 of the superlattice film. The pattern formed by the alternating layers at the edge of the superlattice film can be thought of as a mask for the creation of a slot structure in an etching process. The pattern in this mask is synthetically generated during the deposition process. The slot sizes determined by the individual layer thicknesses and the chemistry of the slot wall is determined by the materials used to form the superlattice film. FIGS. 1 and 2 show schematic diagrams of superlattice films patterned with an array of microcolumnar posts that expose the layer edges 9, 11, 29 and 31. Slot structures 13 and 23 are formed by differentially etching the layers in this pattern occurring at the post edges. To obtain the type of controlled slot structures 13 and 39 shown in FIGS. 1 and 2, it is necessary for the layer being etched to etch more than 10 times faster than the adjacent layer. A more preferred range of chemical selectivity for the etching process is a ratio of 100:1 for the etching rates of adjacent layers.

From the foregoing description, it will be apparent that differentially etched superlattices form a new class of shape selective materials. Variations and modifications of this composition of matter will undoubtedly suggest themselves to those skilled in the art.

It is also clear that several applications of these materials exist in the areas of separations and catalysis. By making the slot width comparable to molecular dimensions of interest; shape and size selective effects can be introduced into separative as well as catalytic processes. Slot width can be made comparable with molecular dimensions either by directly fabricating the desired width or by reducing the effective slot width using a coating formed after the slot is fabricated. Coatings applied to the slot wall which reduce the effective width can either be organic or inorganic. Suitable organic molecules for lining the interior of a slot and reducing the effective width include alcohols, surfactants, silane coupling agents . . . . The organic layer not only reduces the effective width of the two dimensional slot, but also can be used to alter the surface chemistry. For instance, the wall of a slot can be made either hydrophobic or hydrophyllic and exhibit absorption phenomena which are not only size dependent but are also selective to the hydrophobicity of a molecule. If the layer forming the slot end acts as a catalyst, then only reactants with the proper hydrophobic character will be brought to the reaction site, yielding a catalytic process which is both selective with respect to size and functionality of the reactant. Other variations involve applying a coating layer selectively at the slot end to either create a catalytic site or surface functionalization. Catalytic processes occurring at the end of a slot will be geometrically constrained and may tend to suppress undesired reaction channels. For instance, branching reactions occurring during polymerization will be constrained by the slot walls. The microporous superlattices also give new degrees of freedom in chemical process design. Since the active material can be fabricated directly on a substrate several different types of "fixed" bed processes can be envisioned. By making the substrate out of a flexible material such as polyimide, it is possible to make a continuous belt having microporous superlattice material on the surface. This belt can be moved between two tanks of liquids; transporting material trapped in the slots from one tank to another. By absorbing material in one tank and removing it from the slots in another, a continuous separation is produced.

Another separation method can be designed to take advantage of the planar geometry offered by micro-porous superlattices fabricated on substrates. In this case a chromatographic separation column is microfabricated using the micro-porous superlattice as the packing. By microfabricating a flow channel over a micro-porous superlattice it is possible to obtain a micro-bore chromatography column inexpensively made using lithographic fabrication techniques.

The invention will be better understood by reference to the following illustrative examples.

EXAMPLE 1

To demonstrate the fabrication of the absorbing materials of the present inventon, a micro-porous superlattice material was prepared from a semiconductor superlattice consisting of layers of hydrogenated amorphous silicon alternating with layers of hydrogenated amorphous germanium. Alternating layers of hydrogenated amorphous silicon and hydrogenated amorphous germanium were deposited on polished crystalline silicon wafers using an rf plasma assisted chemical vapor deposition process in which the reactive gases pure $SiH_4$ and $GeH_4$ diluted with $H_2$ (1:10) were changed periodically in the plasma reactor without interrupting the plasma. In order to achieve sharp interfaces between the layers, the residence time $T_r$ of gas molecules in the reactor was made to be short compared with the time $T_m$ required to grow a monolayer. The residence time for the gas is $T_r = Vp/F_0p_0$ where V is the volume of the reactor, p is the gas pressure in the reactor and $p_0$ and $F_0$ the pressure and flow rate at STP. The condition $T_r < T_m$ is readily achievable. For instance, in our experiments we use V=3 liters; p=30 m torr; $F_0$=85 cc/min. so that the expected value of $T_r$ is one second. Depositions are performed using an rf power of 5 watts at 13.56 megahertz and $T_m$=3-5 sec. These depositions conditions insure abrupt interfaces between layers in the growing film. Uniformity of the layers and smoothness of the interfaces is determined in part by the deposition temperature; and in the present reactor substrates are placed on the anode and both cathode and anode (6 inch diameter separated by a 2 inch gap) are heated to 180°–220° C. Using this deposition technique films with more than 400 alternating layers of a—Si:H and a—Ge:H were deposited with individual layers having thicknesses of approximately 25 Å. Films were divided in the form of cylindrical posts using a microfabrication technique called natural lithography. (H. W. Deckman and J. H. Dunsmuir, Appl. Phys. Lett. 41, 377 [1982]). In this technique an etch mask is formed from a submonolayer of regularly shaped colloidal particles coated onto the film surface. Colloidal particles are coated as a densely packed random array by inducing an electrostatic attraction between the colloid and film. The colloidal particles used as an etch mask are monodisperse polystyrene spheres (such as can be purchased from Dow Diagnostics) which have a negative surface charge of 1-5 $\mu C/cm^2$ due to a persulfate initiator utilized in an emulsion polymerization process. The a—Si:H/a—Ge:H superlattice acquires a charge similar to that of the sol and a thin interlayer must be deposited to reverse the sign of the surface charge on the superlattice. To create a negative charge on the superlattice, a monolayer of 100 Å colloidal alumina particles is deposited. The colloidal coating is produced by dipping the superlattice film into a pH 5 colloidal alumina sol (0.1% solids) and rinsing off those particles which are not electrostatically bonded to the surface. After excess coating material has been removed, the substrate is dried with the coating fixed on the surface. This coating imparts a positive surface charge which can be used to attract a monolayer of the monodisperse polystyrene latex. The monolayer of polystyrene particles is coated onto the surface in a similar manner by immersing the film into a pH 5 polystyrene latex (0.3% solids) and rinsing off those particles which are not electrostatically bonded onto the surface. After the excess coating material has been removed and the substrate dried, the monolayer of polystyrene particles is used as a lithographic mask in an etching process. Cylindrical posts are created by directionally etching the colloidally coated superlattice with a $CCl_4$ ion beam generated in a Kauffman type ion source and accelerated to 500 electron volts with a current density of 0.5 milliampers per $cm^2$. The ion beam erodes the superlattice approximately 5 times faster than the polystyrene sphere mask creating microscopic cylindrical posts. Height of the post structures (and thus the number of layers exposed) is determined by the etching time. In the present example the $CCl_4$ ion beam eroded the superlattice for a period of ten minutes. Layers exposed at the edge of the cylindrical post structures were differentially etched using hydrogen peroxide. Hydrogen peroxide selectively attacks the germanium layer in the amorphous silicon/amorphous germanium superlattice. To form slots, a densely packed random array of 3000 Å diameter posts was etched for 15 seconds in hydrogen peroxide. The hydrogen peroxide was removed from the etched slots by rinsing in deionized water for 30 seconds followed by a a final rise in isopropyl alcohol. The isopropyl alcohol was then evaporated from the slots leaving free standing slot shaped pores.

Figure 3:
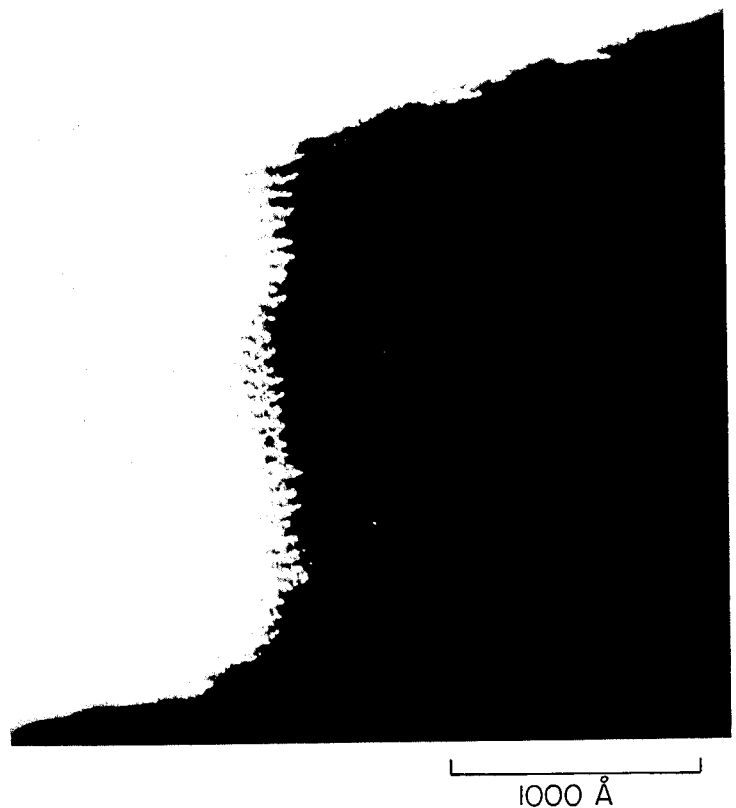
FIG. 3 shows a transmission electron micrograph of the slot shaped pores formed at the perimeter of a 3000 Å diameter post that was etched into an amorphous silicon amorphous germanium superlattice structure. Pores shown in the figure are approximately 30 Å in width.

FIG. 3 shows a transmission electron micrograph of the slot shaped pores formed at the perimeter of a 3000 Å diameter post that was etched into an amorphous silicon amorphous germanium superlattice structure. To view the slots at the perimeter of the posts, a 200 micron wide slice was cut from the substrate on which the superlattice was deposited and aligned in the transmission electron microscope so that the electron beam grazes across the etched surface. The dark bands in the transmission electron micrograph correspond to the amorphous germanium layers while the light bands correspond to amorphous silicon layers. Gaps apparent in the amorphous germanium layers at the edge of the post correspond to the slots etched into the superlattice structure. It is seen that the average width of the slots is determined by the layer spacing in the superlattice, even though the layers defining the slots have curled. Curling of the layers at the edge of an etched slot can be due to either capillary effects occurring during drying of solvent from the etched slot; or high intrinsic stresses in the thin superlattice layers exposed during the etching process. The present invention is meant to include slot structures which have curled as well as slot structure which remain flat. In general, the curling distorts the slot width by less than 30% on average.

EXAMPLE 2

Flat uniformly spaced slotted pores were prepared from an amorphous superlattice consisting of hydrogenated amorphous silicon layers alternating with layers of amorphous silicon dioxide. These layers were deposited on polished crystalline silicon wafers using a deposition technique similar to that described in Example 1. The hydrogenated amorphous silicon layers were grown by flowing $SiH_4$ (pure) through the reactor and the hydrogenated amorphous silicon dioxide layers were grown by flowing $N_2O_2$ diluted with $SiH_4$ (50:1). In this case, abrupt interfaces between layers were obtained by interrupting the plasma in the reactor for 10 seconds while the gasses were changed. Deposited films were divided in the form of cylindrical posts using a method similar to that described in Example 1. A lithographic mask of 2,000 Å diameter monodisperse polystyrene spheres was deposited on the film surface and posts were formed by reactive ion milling for approximately 10 minutes with a 500 ev; 0.3 $mA/cm^2$ beam formed from $CF_4$ gas. Etching with this type ion beam can leave a 50 Å thick fluorocarbon residue on the post which if desired can be removed by etching the posts for approximately 2 minutes with a 0.3 $mA/cm^2$ $O_2$ ion beam. This residue removal technique can also remove the remnants of the sphere mask used to define post structures. If the residue is not removed with an $O_2$ ion beam, the sphere mask remnants are removed by light abrasion applied during a surfactant wash.

Figure 4:
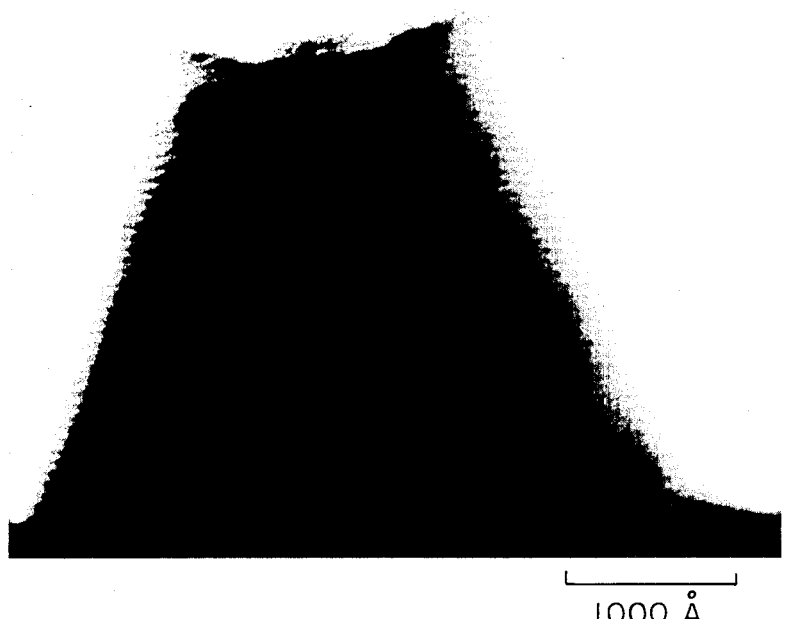
FIG. 4 shows a transmission electron micrograph of layers appearing in post structures formed on a sample grown with a 75 Å repeat distance. The layers are essentially flat and uniform, with the darker layer being amorphous silicon and the lighter layer amorphous silicon dioxide.
Figures 5, 6:
FIG. 5 shows a transmission electron micrograph of slot structures that were etched into posts shown in FIG. 4. The dark central core of the post is the unetched portion of the divided superlattice.
FIG. 6 shows a transmission electron micrograph of a micro-porous superlattice material encased within an 30 Å thick fluorocarbon bag.

FIG. 4 shows a transmission electron micrograph of layers appearing in post structures formed on a sample grown with a 75 Å repeat distance. It is seen that the layers are essentially flat and uniform, with the darker layer being amorphous silicon and the lighter layer amorphous silicon dioxide. The lithographic template formed by the exposed layers at the post edge is clearly visible in FIG. 4, since the fluorocarbon residue from the $CF_4$ etching was removed with an $O_2$ ion beam. Slots were created from this lithographic template by etching the exposed $SiO_2$ layers with buffered hydrofluoric acid (Timetch manufactured by Transine Inc.) for 3.5 minutes. The etch was terminated by immersing the sample in dilute $NH_3OH$, to neutralize the acid. Following the neutralization step, the sample was rinsed in water then isopropyl alcohol and dried in a flowing $N_2$ gas stream. FIG. 5 shows a transmission electron micrograph of slot structures that were etched into posts shown in FIG. 4. The dark central core of the post shown in FIG. 5 is the unetched portion of the divided superlattice. Dark bands across the post correspond to the unetched amorphous silicon layers while light bands at the exterior of the dark central core correspond to etched slot interiors. The slots shown in the micrograph extend 500 Å in from the post structures and are flat and uniform.

When the residue from $CF_4$ etching is not removed prior to etching, the type of slotted posts shown in FIG. 6 are obtained. In this case the etched slotted post structure is encased in a 30 Å thick fluorocarbon bag. The slotted post structures are readily visible through the thin polymeric bag.

EXAMPLE 3

The method of Example 2 was used to divide a deposited amorphous hydrogenated silicon/amorphous hydrogenated silicon dioxide superlattice into 2,000 Å diameter posts. The amorphous silicon layer (rather than the amorphous silicon dioxide layer) was etched away using $XeF_2$ as an etchant. $XeF_2$ was delivered to the surface of the divided superlattice as a gas at a pressure of 30 millitorr. Because $XeF_2$ is a highly selective silicon etchant, the divided superlattice was cleaned with a 500 ev (0.25 ma/cm$^2$) argon ion beam for one minute prior to etching. The etching process was conducted in the vacuum system used to generate the ion beam, so that samples were not exposed to air, between the cleaning and etching steps. the $XeF_2$ etching process was conducted for a period of 10 minutes resulting in a micro-porous superlattice material for which slots are generated by removal of an amorphous silicon layer.

B. Absorption of Molecules by Superlattice Material

Figure 7:
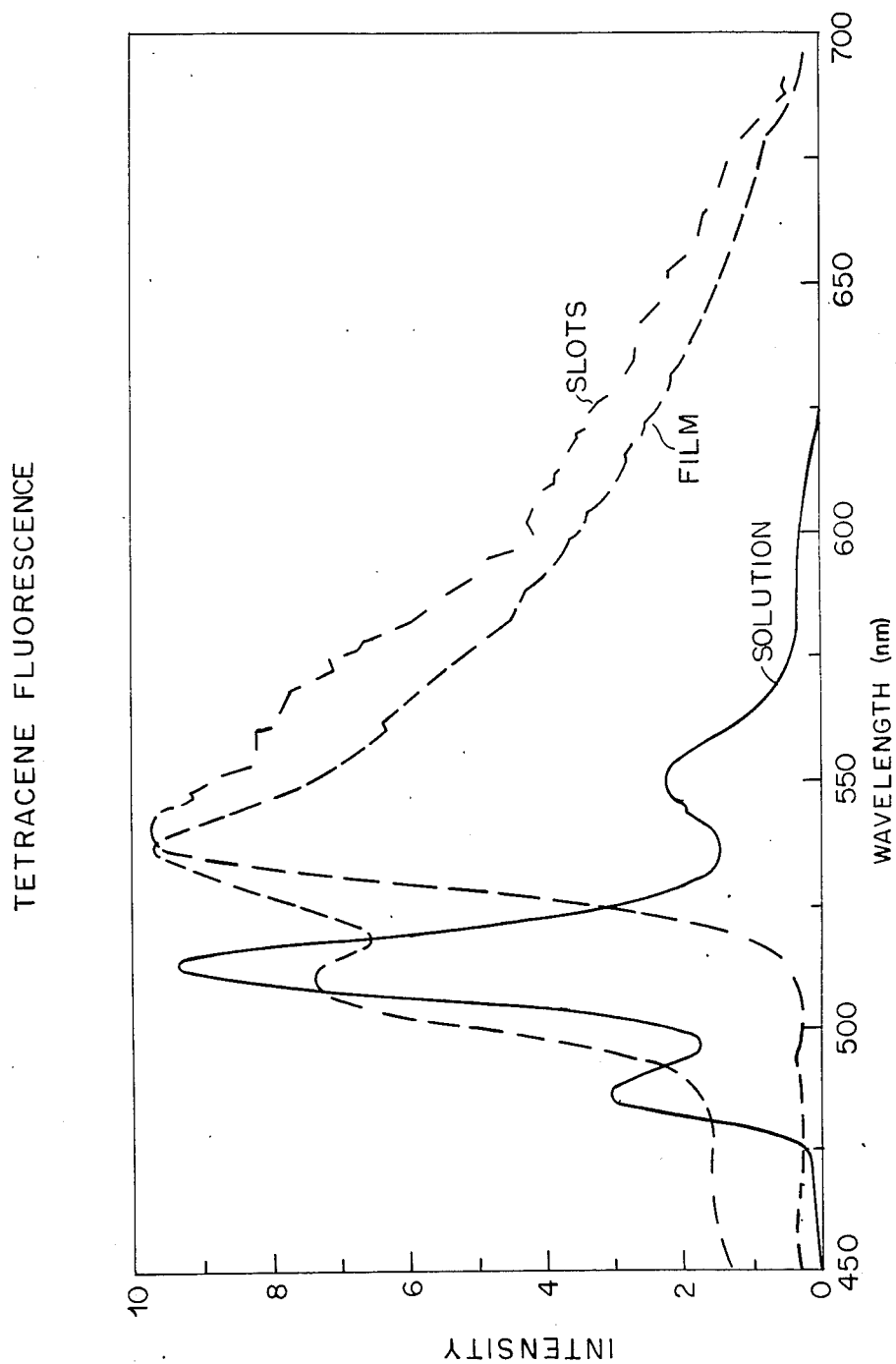
FIG. 7 shows the fluorescence spectra of tetracene molecules trapped in slots, in solution, and in a solid film.

Micropores were prepared from a—Si:H/a—SiO$_x$:H superlattices using the method as described above. In this method, a microporous material is created by breaking the superlattice film up in a manner which exposes edges of the thin film layers followed by a selective etching of one or more of the thin film layers. In the present invention, both $XeF_2$ and HF were used as selective etches. The deposited superlattice was divided in the form of individual posts using a lithographic patterning process. The "posts" were not separated from the silicon substrate. The slots etched into the posts were treated in chromic sulfuric acid followed by rinses in distilled water, HCl and isopropyl alcohol. They were then dipped immediately into a solution of the organic molecules. After a few minutes, the slots were removed and rinsed quickly in alcohol to remove molecules from the surface. Alcohols used in preparation of the slots include isopropyl, ethyl, methyl and butyl alcohol. After rinsing in alcohol, the slots were blown dry with nitrogen to remove excess alcohol and prevent water condensation in the evaporating alcohol layer. Molecules inside the pores were detected using fluorescence spectroscopy. FIG. 7 shows the fluorescence spectra of tetracene molecules trapped in slots, in a solid and in solution. It can be seen that the slot spectrum is intermediate between the others; it retains the 510 nm peak characteristic of individual molecules yet still has considerable intermolecular interaction as evidenced by the long red tail. Quantitative comparisons of the luminescence intensities shows that tetracene occupies roughly 50% of the pore volume.

Figure 8:
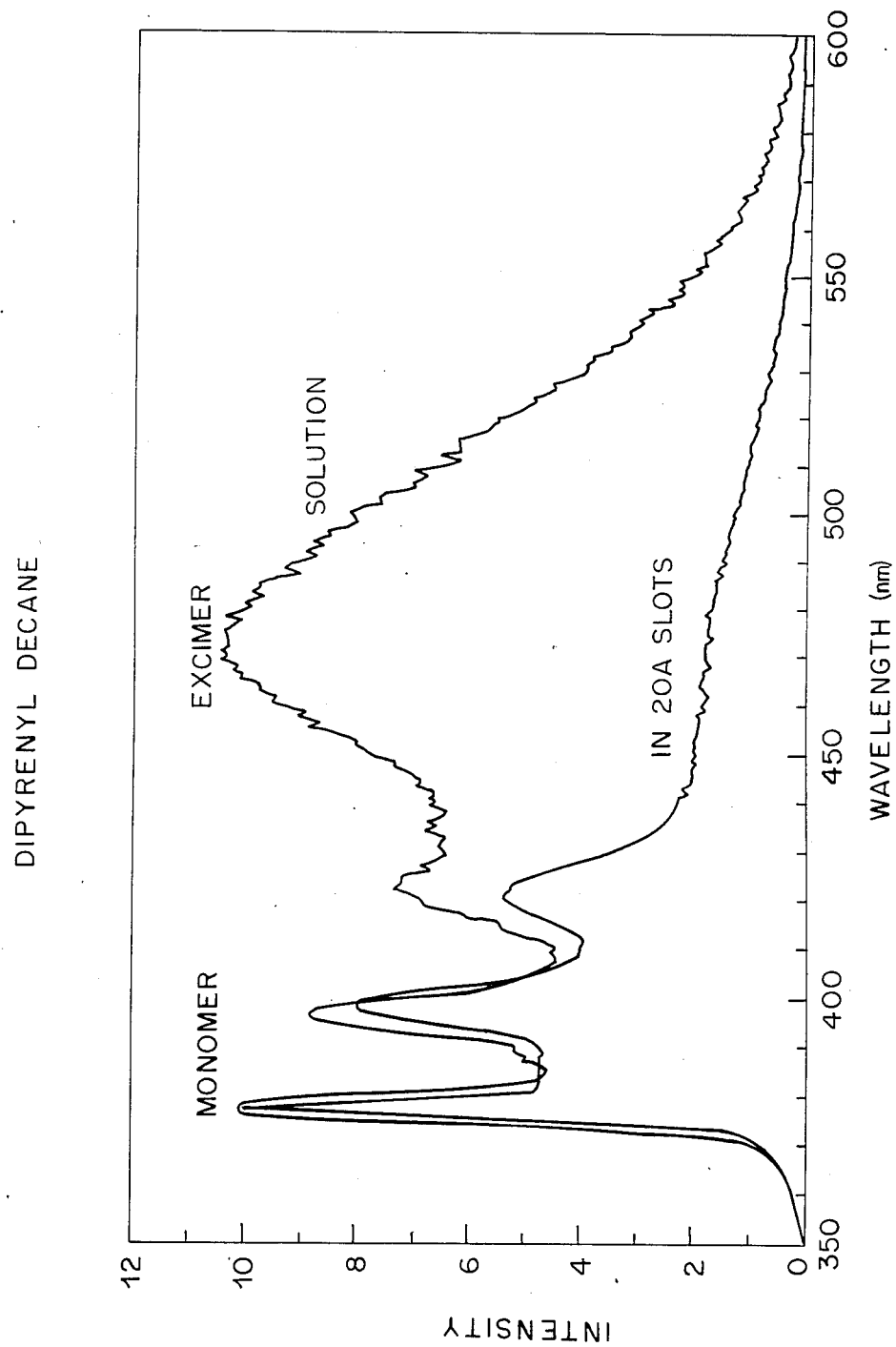
FIG. 8 shows the fluorescence spectra of dipyrenyl decane molecules trapped in slots, and in solution.

FIG. 8 shows the fluorescence spectrum of dipyrenyl decane molecules trapped in slots and in solution. The slots were prepared as in Example 2 above but they were only 20 Å wide. This data shows that the dipyrenyl decane molecules in the micropores do not combine to form dimers or excimers (see, e.g., J. B. Birks, Photophysics of Aromatic Molecules, Wiley-Interscience, London, 1970) as they do in solution, as evidenced by the weakness of the 470 nm excimer band. This is due to the confining effect of the slot walls.

Figure 9A:
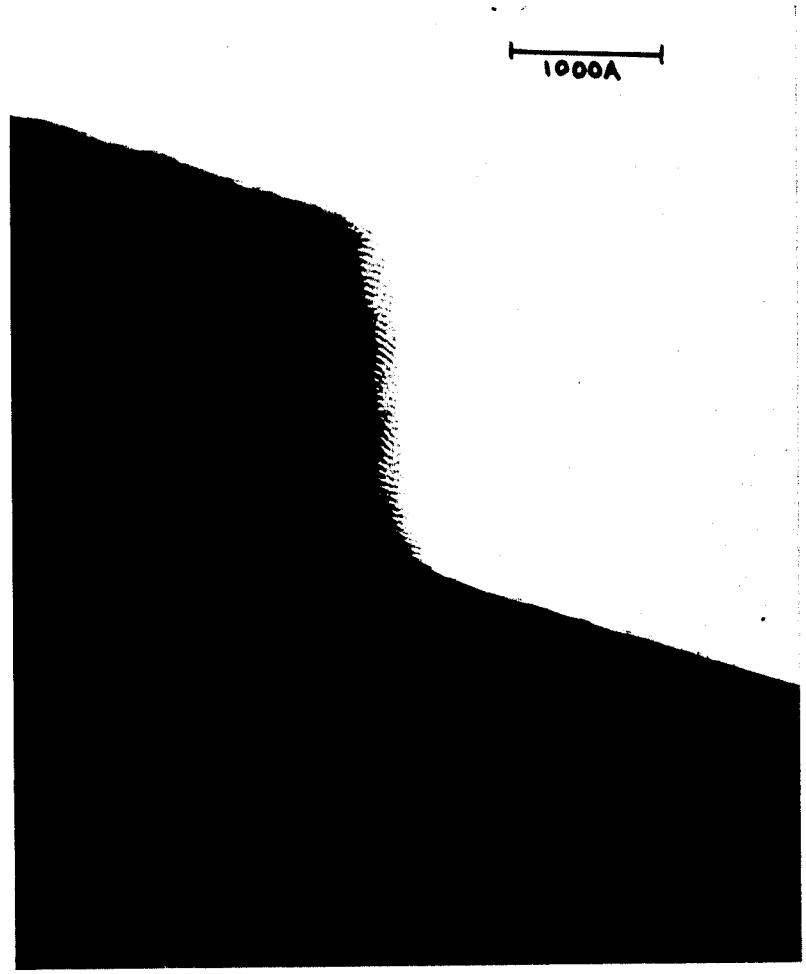
FIG. 9 shows a micrograph of a slot structure before (a) and after (b) the absorption of molecules.
Figure 9B:

For such a large fractional filling of the slots, the appearance of slots in transmission electron microscopy should be quite different before and after filling with molecules. FIGS. 9a and 9b show how the appearance of slots change after absorbing molecules so that a large fraction of the available pore volume is filled. FIG. 9a shows slots etched into a Si/SiO$_2$ superlattice using HF and FIG. 9b shows the appearance of the slots after absorbing dipyrenyl decane into slots. The differences seen in the micrographs would not be apparent unless a large fraction of the slot structure were filled with molecules.

To further establish that the molecules observed in the fluorescence spectra were located in the interior of the slot structures, the following experiment was conducted. Tetracene molecules were absorbed into slot structures and excess material was removed by rinsing with isopropyl alcohol for 20 seconds and blowing off the excess. The sample was then ion beam etched with oxygen for 10 seconds using a 500 eV, 0.3 mA/cm$^2$ beam. This selectively removes organic material on the exterior surface of the slot structures without substantially affecting the slots or the material contained therein. The fluorescence spectra was observed to be the same before and after the milling, showing that the molecules are primarily in the slots.

Many molecules were observed to adsorb into the slots, including anthracene, tetracene, perylene, chrysene, and Rhodamine B. Rubrene, on the other hand, was not observed to adsorb into 20 Å slots. This we attribute to the large size (8 benzene rings) and three dimensional character of the molecule.

The strength of the absorption was observed to vary with the molecule absorbed and the micropore material. Some molecules, notably tetracene, were observed to desorb into alcohol solutions only after several hours, a very long time by usual desorption standards. Other molecules desorbed very quickly, faster than could be measured.

Due to the preparation method, these micropores were presumably lined with OH functionalities, and are capable ot separations based on the surface chemistry. Because of the almost unlimited variety of materials that can be made into superlattice micropores, the number of surface treatments which can be applied is much larger than is possible in silica gels, as an example. By making the slot width comparable to molecular dimensions of interest, shape and size selective effects can be introduced into separative processes. Slot width can be made comparable with molecular dimensions either by directly fabricating the desired width or by reducing the effective slot width using a coating formed after the slot is fabricated. Coatings applied to the slot wall which reduce the effective width can either be organic or inorganic. Suitable organic molecules for lining the interior of a slot and reducing the effective width include alcohols, surfactants, silane coupling agents . . . . The organic layer not only reduces the effective width of the two dimensional slot, but also can be used to alter the surface chemistry. For instance, the wall of a slot can be made either hydrophobic or hydrophyllic and exhibit absorption phenomena which are not only size dependent but are also selective to the hydrophobocity of a molecule. In existing zeolites the pores are too small to take such a lining without clogging.

Larger pores are useful for separations of polymers. Superlattice micropores are much more monodisperse in pore size than existing systems. It might also be possible to use the two-dimensinal character of the slots to make shape selective separations, e.g., to separate branched from linear polymers.

Since the active material can be fabricated directly on a substrate, several different new types of "fixed" bed separative processes can be envisioned. As stated above, by making the substrate out of a flexible material such as polyimide, it is possible to make a continuous belt having microporous superlattice material on the surface. This belt can be moved between two tanks of liquids, transporting material trapped in the slots from one tank to another. By absorbing material in one tank and removing it from the slots in another, a continuous separation is produced.

Another separation method can be designed to take advantage of the planar geometry, offered by microporous superlattices fabricated on substrates. In this case a chromatographic separation column is microfabricated using the microporous superlattice as the packing. By microfabricating a flow channel over a microporous superlattice, it is possible to obtain a micropore chromatography column inexpensively made using lithographic fabrication techniques.

What is claimed is:

1. A process for absorbing a molecular species from a medium of a liquid or a gas comprising contacting said medium with a superlattice which includes multilayered material having layers which extend laterally with different dimensions so as to provide two dimensional slots between said layers within said multilayered material.

2. The process of claim 1 wherein said molecular species is organic.

3. The process of claim 2 wherein said molecular species is a hydrocarbon.

4. The process of claim 3 wherein said molecular species is aromatic.

5. The process of claim 2 wherein said molecular species is selected from the group consisting of tetracene, pyrene, anthracene, napthalene, rubene and dipyrenyl decane.

6. The process of claim 1 wherein said contacting step separates a molecular species from said medium.

7. The process of claim 6 further comprising the step of removing said superlattice from said medium thereby removing said molecular species.

8. The process of claim 7 wherein said absorption is shape selective.

9. The process of claim 7 wherein said absorption is size selective.

10. The process of claim 9 wherein a smaller molecule is separated from a larger molecule by the smaller molecule preferentially entering said slots.

* * * * *